United States Patent
Yanagawa et al.

(10) Patent No.: US 9,446,997 B2
(45) Date of Patent: Sep. 20, 2016

(54) METHOD FOR PRODUCING AROMATIC HYDROCARBONS

(75) Inventors: Shinichiro Yanagawa, Tokyo (JP); Ryoji Ida, Tokyo (JP); Masahide Kobayashi, Tokyo (JP)

(73) Assignee: JX Nippon Oil & Energy Corporation, Tokyo (JP)

( * ) Notice: Subject to any disclaimer, the term of this patent is extended or adjusted under 35 U.S.C. 154(b) by 251 days.

(21) Appl. No.: 13/822,487

(22) PCT Filed: Sep. 14, 2011

(86) PCT No.: PCT/JP2011/070946
§ 371 (c)(1),
(2), (4) Date: Mar. 12, 2013

(87) PCT Pub. No.: WO2012/036186
PCT Pub. Date: Mar. 22, 2012

(65) Prior Publication Data
US 2013/0172639 A1    Jul. 4, 2013

(30) Foreign Application Priority Data
Sep. 14, 2010   (JP) .................................. 2010-205666

(51) Int. Cl.
*C07C 4/06*      (2006.01)
*B01J 37/00*    (2006.01)
(Continued)

(52) U.S. Cl.
CPC ................ *C07C 4/06* (2013.01); *B01J 23/882* (2013.01); *B01J 29/06* (2013.01); *B01J 29/061* (2013.01); *B01J 29/405* (2013.01); *B01J 35/023* (2013.01); *B01J 37/0009* (2013.01); *B01J 37/0045* (2013.01); *C01B 39/065* (2013.01); *C01B 39/40* (2013.01); *C07C 4/18* (2013.01);
(Continued)

(58) Field of Classification Search
None
See application file for complete search history.

(56) References Cited

U.S. PATENT DOCUMENTS

| | | |
|---|---|---|
| 3,008,895 A | 11/1961 | Hansford et al. |
| 4,097,367 A | 6/1978 | Haag et al. |

(Continued)

FOREIGN PATENT DOCUMENTS

| | | |
|---|---|---|
| CN | 1311289 A | 9/2001 |
| GB | 1287722 A | 9/1972 |

(Continued)

OTHER PUBLICATIONS

Vasant P. Thakkar, Suheil F. Abdo, Visnja A. Gembicki and James F. Mc Gehee. "LCO Upgrading a Novel Approach for Greater Added Value and Improved Returns". © 2005 UOP LLC.*

(Continued)

*Primary Examiner* — In Suk Bullock
*Assistant Examiner* — Ali Z Fadhel
(74) *Attorney, Agent, or Firm* — Panitch Schwarze Belisario & Nadel LLP

(57) ABSTRACT

Provided is a method for producing aromatic hydrocarbons, by which a feedstock containing a hydrogenation-treated oil of a thermally cracked heavy oil obtainable from an ethylene production apparatus is brought into contact with a catalyst for monocyclic aromatic hydrocarbon production containing a crystalline aluminosilicate, and thereby aromatic hydrocarbons are produced. A raw material having an end point of the distillation characteristics of 400° C. or lower is used as the feedstock. The contact between the feedstock and the catalyst for monocyclic aromatic hydrocarbon production is carried out at a pressure of 0.1 MPaG to 1.5 MPaG.

11 Claims, 1 Drawing Sheet

(51) Int. Cl.
  *C10G 29/20* (2006.01)
  *C10G 57/00* (2006.01)
  *C10G 65/04* (2006.01)
  *C10G 69/06* (2006.01)
  *C07C 4/18* (2006.01)
  *B01J 23/882* (2006.01)
  *B01J 29/06* (2006.01)
  *B01J 29/40* (2006.01)
  *B01J 35/02* (2006.01)
  *C01B 39/40* (2006.01)
  *C01B 39/06* (2006.01)
  *C10G 35/095* (2006.01)
  *C10G 45/68* (2006.01)
  *C10G 69/08* (2006.01)
  *C10G 9/00* (2006.01)
  *C10G 51/04* (2006.01)
  *C10G 63/04* (2006.01)
  *C10G 69/04* (2006.01)

(52) U.S. Cl.
  CPC .......... *C10G 9/00* (2013.01); *C10G 29/205* (2013.01); *C10G 35/095* (2013.01); *C10G 45/68* (2013.01); *C10G 51/04* (2013.01); *C10G 57/005* (2013.01); *C10G 63/04* (2013.01); *C10G 65/046* (2013.01); *C10G 69/04* (2013.01); *C10G 69/06* (2013.01); *C10G 69/08* (2013.01); *B01J 2229/186* (2013.01); *C07C 2529/40* (2013.01); *C10G 2300/301* (2013.01); *C10G 2300/4012* (2013.01); *C10G 2300/4018* (2013.01); *C10G 2400/30* (2013.01); *Y02P 20/52* (2015.11)

(56) References Cited

U.S. PATENT DOCUMENTS

| 4,305,808 | A | | 12/1981 | Bowes et al. | |
|---|---|---|---|---|---|
| 4,585,545 | A | * | 4/1986 | Yancey et al. | 208/74 |
| 4,676,887 | A | | 6/1987 | Fischer et al. | |
| 5,981,418 | A | * | 11/1999 | Drake et al. | 502/64 |
| 6,124,515 | A | * | 9/2000 | Wu et al. | 585/418 |
| 6,569,316 | B2 | * | 5/2003 | Winter | 208/77 |
| 2007/0293714 | A1 | | 12/2007 | Long et al. | |

FOREIGN PATENT DOCUMENTS

| JP | 56-157488 | A | | 12/1981 |
|---|---|---|---|---|
| JP | 61-148295 | A | | 7/1986 |
| JP | 61-283687 | A | | 12/1986 |
| JP | 02-258893 | A | | 10/1990 |
| JP | 03-002128 | A | | 1/1991 |
| JP | 03-026791 | A | | 2/1991 |
| JP | 03-052993 | A | | 3/1991 |
| JP | 04-030436 | B | | 5/1992 |
| JP | 04-030437 | B | | 5/1992 |
| JP | 05-112785 | A | | 5/1993 |
| JP | 2908959 | B2 | | 4/1999 |
| JP | 2007-154151 | A | | 6/2007 |
| JP | 2007154151 | A | * | 6/2007 |
| JP | 2007530266 | A | | 11/2007 |
| JP | 2008-074998 | A | | 4/2008 |
| JP | 4740396 | B2 | | 5/2011 |
| WO | 0104785 | A2 | | 1/2001 |
| WO | 2009119390 | A1 | | 10/2009 |
| WO | 2011118753 | A1 | | 9/2011 |

OTHER PUBLICATIONS

Office Action issued Apr. 3, 2014 in CN Application No. 201180043784.0.
Int'l Search Report issued Nov. 15, 2011 in Int'l Application No. PCT/JP2011/070946.
Office Action issued Sep. 28, 2015 in EP Application No. 11825186.7.

* cited by examiner

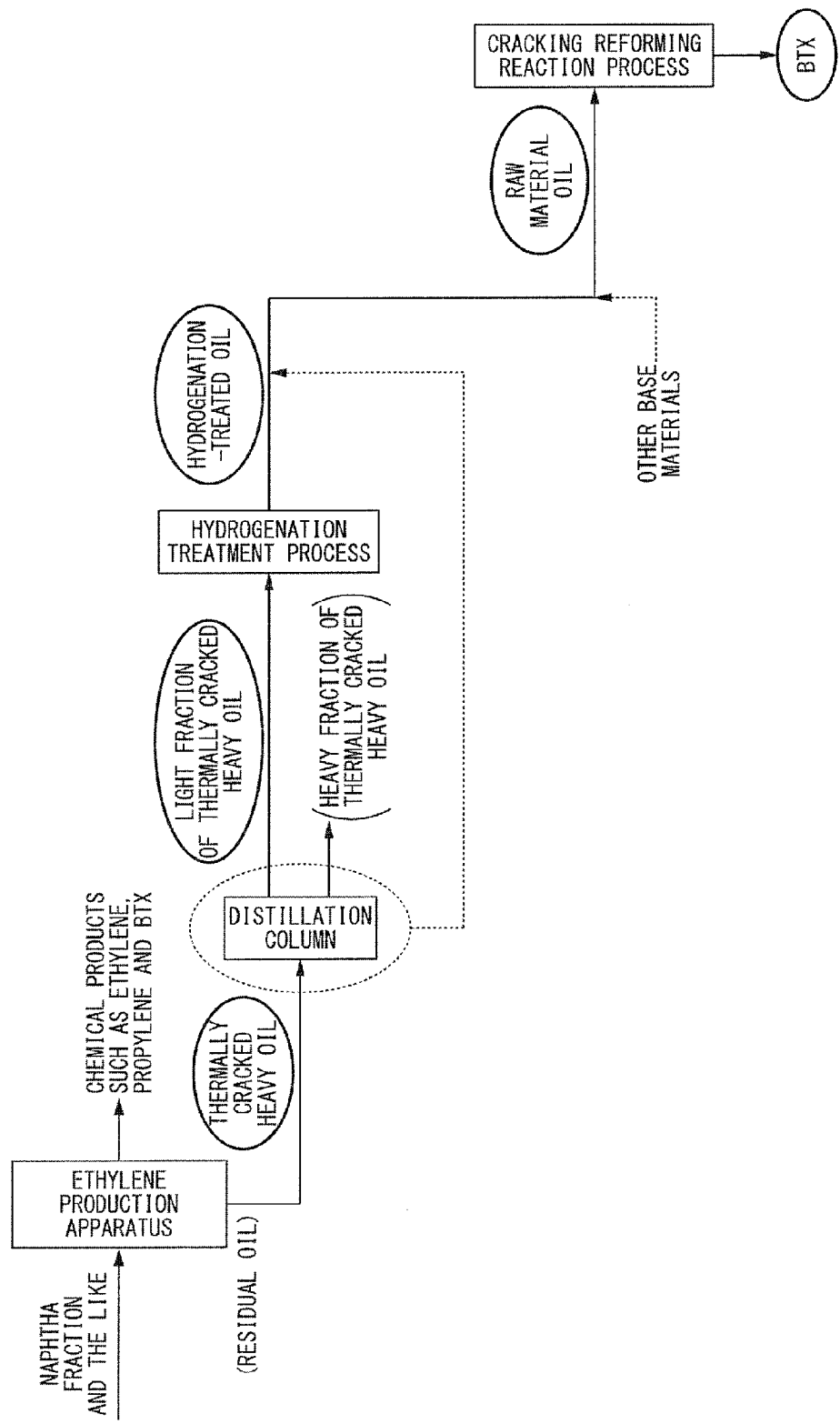

METHOD FOR PRODUCING AROMATIC HYDROCARBONS

CROSS-REFERENCE TO RELATED APPLICATION

This application is a Section 371 of International Application No. PCT/JP2011/070946, filed Sep. 14, 2011, which was published in the Japanese language on Mar. 22, 2012, under International Publication No. WO 2012/036186 A1, and the disclosure of which is incorporated herein by reference. Priority is claimed from Japanese Patent Application No. 2010-205666, filed Sep. 14, 2010, the disclosure of which is incorporated herein by reference.

BACKGROUND ART

Light cycle oil (hereinafter, referred to as "LCO"), which is a cracked light oil produced by a fluid catalytic cracking (hereinafter, referred to as "FCC") apparatus, and the like contain many polycyclic aromatic components, and so far, light cycle oil has been used primarily as light oil/heavy oil fractions. In recent years, there has been a demand for a technology of efficiently producing monocyclic aromatic hydrocarbons having 6 to 8 carbon atoms (for example, benzene, toluene, and crude xylene (xylene containing a small amount of ethylbenzene or the like); hereinafter, these will be collectively referred to as "BTX") having a high added value, which uses LCO and the like as a raw material, and can be utilized as high octane value gasoline base materials or petrochemical raw materials.

Regarding the method for producing BTX from a polycyclic aromatic component, for example, methods described below and the like are known.

(1) A method of subjecting a hydrocarbon containing a polycyclic aromatic component to hydrogenation-cracking in a single stage (Patent Documents 1 and 2).

(2) A method of hydrogenation-treating a hydrocarbon containing a polycyclic aromatic component in an earlier stage and then subjecting the product to hydrogenation-cracking in a later stage (Patent Documents 3 to 5).

(3) A method of directly converting a hydrocarbon containing a polycyclic aromatic component to BTX by using a zeolite catalyst (Patent Document 6).

(4) A method of converting a mixture of a hydrocarbon containing a polycyclic aromatic component and light hydrocarbons having 2 to 8 carbon atoms to BTX by using a zeolite catalyst (Patent Documents 7 and 8).

However, in the methods of (1) and (2), addition of molecular hydrogen at a high pressure is essential, and there is a problem that large hydrogen consumption is needed. Furthermore, under the conditions of the hydrogenation treatment, an LPG fraction and the like are produced to a large extent as side products, so that not only is energy required for separation thereof, but also the raw material efficiency is also decreased.

In the method of (3), conversion of the polycyclic aromatic component is not sufficiently achieved.

The method of (4) is a method of enhancing the thermal balance by combining a BTX production technology using light hydrocarbons as raw materials and a BTX production technology using a hydrocarbon containing a polycyclic aromatic component as a raw material, and this method does not always increase the yield of BTX from the polycyclic aromatic component.

Also available as a material containing a polycyclic aromatic component at a high concentration such as LCO, is a cracked heavy oil (thermally cracked heavy oil) that is obtained from an ethylene production apparatus. This cracked heavy oil is mostly used as a fuel for boilers in a Combinat. Regarding other utilization methods for the cracked heavy oil, it is known that an ethylene heavy end is treated in the presence of a solid acid catalyst in a hydrogen atmosphere, and thus a modified pitch from which the light-boiling fraction obtainable up to 500° C. is excluded, which is used as a raw material of carbon fibers, may be obtained (Patent Documents 9 and 10).

However, a method for producing, at a high yield, BTX by using such a thermally cracked heavy oil as a feedstock is not known.

PRIOR ART DOCUMENTS

Patent Documents

[Patent Document 1] Japanese Unexamined Patent Application, First Publication No. S61-283687
[Patent Document 2] Japanese Unexamined Patent Application, First Publication No. S56-157488
[Patent Document 3] Japanese Unexamined Patent Application, First Publication No. S61-148295
[Patent Document 4] Great Britain Patent No. 1287722
[Patent Document 5] Japanese Unexamined Patent Application, First Publication No. 2007-154151
[Patent Document 6] Japanese Unexamined Patent Application, First Publication No. H03-2128
[Patent Document 7] Japanese Unexamined Patent Application, First Publication No. H03-52993
[Patent Document 8] Japanese Unexamined Patent Application, First Publication No. H03-26791
[Patent Document 9] Japanese Examined Patent Application Publication No. H04-30436
[Patent Document 10] Japanese Examined Patent Application Publication No. H04-30437

DISCLOSURE OF INVENTION

Technical Problem

The invention provides a method for efficiently producing BTX from a feedstock including a hydrogenation-treated oil of a thermally cracked heavy oil obtainable from an ethylene production apparatus, without causing molecular hydrogen to co-exist.

Solution to Problem

The inventors conducted thorough research so as to solve the problems described above, and as a result, the inventors found that BTX can be efficiently produced by using a feedstock including a hydrogenation-treated oil of a thermally cracked heavy oil that is obtainable from an ethylene production apparatus, and bringing the feedstock into contact with a catalyst containing a crystalline aluminosilicate at a low pressure in the absence of molecular hydrogen to react therewith. Thus, the inventors finally completed the invention.

That is, the method for producing aromatic hydrocarbons (BTX) of the invention includes:

a step of obtaining a thermally cracked heavy oil from an ethylene production apparatus;

a step of hydrogenation-treating the thermally cracked heavy oil to obtain a hydrogenation-treated oil; and a cracking reforming reaction step of bringing a feedstock including the hydrogenation-treated oil into contact with a catalyst for monocyclic aromatic hydrocarbon production containing a crystalline aluminosilicate, wherein a feedstock of which the end point of the distillation characteristics is 400° C. or lower is used as the feedstock, and in the cracking reforming reaction step, the reaction pressure employed when the feedstock and the catalyst for monocyclic aromatic hydrocarbon production are brought into contact to react therewith, is set to 0.1 MPaG to 1.5 MPaG.

The hydrogenation-treated oil is preferably such that the content of polycyclic aromatic hydrocarbons having 2 or more rings is 50 mass % or less, and the content of monocyclic aromatic hydrocarbons is 30 mass % or more.

The hydrogenation-treated oil preferably has a content of hydrocarbons having an indane skeleton and an indene skeleton of 5 mass % or more.

The step of obtaining the hydrogenation-treated oil preferably includes a process of separating by distillation the thermally cracked heavy oil; and a process of hydrogenation-treating the thermally cracked heavy oil thus separated by distillation in which hydrogenation treatment is performed by using a catalyst for hydrogenation treatment in the presence of hydrogen, under the conditions of a hydrogen partial pressure of 0.7 MPa to 20 MPa, a LHSV of 0.05 $h^{-1}$ to 2 $h^{-1}$, a reaction temperature of 200° C. to 450° C., and a hydrogen/oil ratio of 100 NL/L to 2000 NL/L.

The step of obtaining the hydrogenation-treated oil preferably includes a process of hydrogenation-treating the thermally cracked heavy oil by using a catalyst for hydrogenation treatment in the presence of hydrogen, under the conditions of a hydrogen partial pressure of 0.7 MPa to 20 MPa, a LHSV of 0.05 $h^{-1}$ to 2 $h^{-1}$, a reaction temperature of 200° C. to 450° C., and a hydrogen/oil ratio of 100 NL/L to 2000 NL/L; and a process of separating by distillation the hydrogenation-treated thermally cracked heavy oil.

The catalyst for hydrogenation treatment is preferably a catalyst obtainable by supporting at least one metal selected from the metals of Group 6 of the Periodic Table of Elements in an amount of 10 mass % to 30 mass % and at least one metal selected from the metals of Group 8 to Group 10 of the Periodic Table of Elements in an amount of 1 mass % to 7 mass %, relative to the total catalyst mass, on an inorganic carrier containing aluminum oxide.

The at least one metal selected from the metals of Group 6 of the Periodic Table of Elements is preferably molybdenum and/or tungsten, and the at least one metal selected from the metals of Group 8 to Group 1.0 of the Periodic Table of Elements is cobalt and/or nickel.

The catalyst for monocyclic aromatic hydrocarbon production preferably contains gallium and/or zinc.

The catalyst for monocyclic aromatic hydrocarbon production preferably contains phosphorus.

Advantageous Effects of Invention

According to the method for producing aromatic hydrocarbons of the invention, BTX can be efficiently produced from a feedstock containing a hydrogenation-treated oil of a thermally cracked heavy oil obtainable from an ethylene production apparatus, without causing molecular hydrogen to co-exist.

BRIEF DESCRIPTION OF THE DRAWINGS

FIG. 1 is a diagram for explaining an embodiment of the method for producing aromatic hydrocarbons of the invention.

BEST MODE FOR CARRYING OUT THE INVENTION

Hereinafter, the method for producing aromatic hydrocarbons of the invention will be described in detail by referring to the drawings. FIG. 1 is an explanatory diagram of an embodiment of the method for producing aromatic hydrocarbons of the invention.

The method for producing aromatic hydrocarbons of the present embodiment is, as shown in FIG. 1, a method for producing BTX by bringing a feedstock including a hydrogenation-treated oil of a thermally cracked heavy oil obtainable from an ethylene production apparatus into contact with a catalyst for monocyclic aromatic hydrocarbon production containing a crystalline aluminosilicate to react therewith, wherein a raw material of which the end point of the distillation characteristics is 400° C. or lower is used as the feedstock, and the contact between the feedstock and the catalyst for monocyclic aromatic hydrocarbon production is carried out at a pressure of 0.1 MPaG to 1.5 MPaG.

(Feedstock)

The feedstock related to the method for producing aromatic hydrocarbons of the present embodiment is an oil including a hydrogenation-treated oil of a thermally cracked heavy oil obtainable from an ethylene production apparatus, and it is necessary that the end point of the distillation characteristics be 400° C. or lower. When the end point is set to 400° C. or lower, in the cracking reforming reaction step based on the contact and reaction with a catalyst for monocyclic aromatic hydrocarbon production, the BTX yield can be increased. Furthermore, in order to further increase the BTX yield, it is preferable to set the end point to 350° C. or lower, and it is more preferable to set the end point to 300° C. or lower. The lower limit of the end point is preferably 200° C. to 300° C. Meanwhile, there are no particular limitations on the distillation characteristics other than the end point, but in order to efficiently produce BTX, preferably the 1.0 vol % distillation temperature (T10) is from 1.40° C. to 220° C., and the 90 vol % distillation temperature (T90) is from 220° C. to 380° C.; and more preferably T10 is from 160° C. to 200° C., and T90 is from 240° C. to 350° C.

Here, the distillation characteristics are measured according to the "Distillation test method for petroleum products" stipulated in JIS K 2254.

Meanwhile, the feedstock related to the method for producing aromatic hydrocarbons of the present embodiment may also include another base material as long as the feedstock includes a hydrogenation-treated oil of a thermally cracked heavy oil obtainable from an ethylene production apparatus. The other base material that is added to a hydrogenation-treated oil will be described below (Thermally Cracked Heavy Oil Obtainable from Ethylene Production Apparatus)

The thermally cracked heavy oil obtainable from an ethylene production apparatus (hereinafter, also referred to as a thermally cracked heavy oil) in the present embodiment is a residual oil obtainable from an ethylene production apparatus which produces chemical products such as ethylene, propylene and BTX by thermally cracking a raw material such as a naphtha fraction or a kerosene/diesel oil fraction, and the thermally cracked heavy oil may also be referred to as Heavy Aromatic Residue oil (HAR oil). Examples of the ethylene production apparatus include a steam cracker (also called a steam cracking apparatus). There are no particular limitations on the raw material of the ethylene production apparatus, but usually a raw material having 80% or more of a petroleum-derived naphtha fraction is used. Regarding raw materials other than a naphtha fraction, diesel oil, cracked gasoline, cracked diesel oil, desulfurized diesel oil and the like can be used.

Regarding the operation conditions for the ethylene production apparatus that produces chemical products such as ethylene and propylene by thermally cracking a raw material such as a naphtha fraction, general conditions can be used, and there are no particular limitations. For example, a method of combining a raw material together with diluting steam at a thermal cracking reaction temperature of 770° C. to 850° C. and a retention time (reaction time) of 0.1 seconds to 0.5 seconds may be used. If the thermal cracking temperature is lower than 770° C., cracking does not proceed, and a target product may not be obtained. Therefore, the lower limit of the thermal cracking reaction temperature is more preferably 775° C. or higher, and even more preferably 780° C. or higher. On the other hand, if the thermal cracking temperature is higher than 850° C., the gas production amount rapidly increases, and the operation of the steam cracker is hindered. Therefore, the upper limit of the thermal cracking reaction temperature is more preferably 845° C. or lower, and even more preferably 840° C. or lower. The steam/raw material (mass ratio) is preferably 0.2 to 0.9, more preferably 0.25 to 0.8, and even more preferably 0.3 to 0.7. The retention time (reaction time) of the raw material is more preferably 0.15 seconds to 0.45 seconds, and even more preferably 0.2 seconds to 0.4 seconds.

(Characteristics of Thermally Cracked Heavy Oil)

The characteristics of the thermally cracked heavy oil in the present embodiment are not particularly defined, but it is preferable that the thermally cracked heavy oil have the following characteristics.

In regard to a distillation test, a thermally cracked heavy oil having a 10 vol % distillation temperature (T10) in the range of from 190° C. to 230° C., a 50 vol % distillation temperature (T50) in the range of from 210° C. to 300° C., a 90 vol % distillation temperature (T90) in the range of from 480° C. to 540° C., and an end point (EP) in the range of from 550° C. to 650° C. is preferably used. If the end point exceeds 650° C., the content of poisoning materials against a catalyst such as a heavy metal increases, and the service life of the catalyst is greatly decreased, which is not preferable.

Furthermore, it is preferable that the density of the thermally cracked heavy oil at 15° C. be from 1.03 g/cm$^3$ to 1.08 g/cm$^3$, the dynamic viscosity at 50° C. be from 20 mm$^2$/s to 45 mm$^2$/s, the sulfur content (sulfur fraction) be from 200 ppm by mass to 700 ppm by mass, the nitrogen content (nitrogen fraction) be 20 ppm by mass or less, and the aromatic component be 80 vol % or more.

Meanwhile, when the thermally cracked heavy oil is subjected to a hydrogenation treatment as will be described below, the thermally cracked heavy oil may be directly hydrogenation-treated. Furthermore, as shown in FIG. 1, the thermally cracked heavy oil may be separated by distillation in advance at a predetermined cut temperature (for example, the boiling point of 400° C.), and then the light fraction (light oil fraction) of the thermally cracked heavy oil thus obtainable may be hydrogenation-treated.

Here, the distillation test means measurement made according to the "Distillation testing methods for petroleum products" stipulated in JIS K 2254. The density at 15° C. means a density measured according to the "Oscillation type density test method" of "Crude oil and petroleum products—Density testing methods and tables for density/mass/volume conversion (excerpt)" stipulated in JIS K 2249. The dynamic viscosity at 50° C. means a value obtainable according to JIS K 2283 "Crude oil and petroleum products—Dynamic viscosity testing methods and viscosity index calculation methods". The sulfur content means a sulfur content measured according to the "Radiation type excitation method" of "Crude oil and petroleum products—Sulfur component testing methods" stipulated in JIS K 2541-1992. The nitrogen content means a nitrogen content measured according to JIS K 2609 "Crude oil and petroleum products—Nitrogen component testing methods". The aromatic content means the content of all aromatic components measured by the Japan Petroleum Institute Standards JPI-5S-49-97 "Petroleum products—Hydrocarbon type testing methods—High performance liquid chromatography".

(Hydrogenation Treatment of Thermally Cracked Heavy Oil)

The thermally cracked heavy oil obtainable from an ethylene production apparatus usually has a very large content of aromatic hydrocarbons. Thus, in the method for producing aromatic hydrocarbons of the present embodiment, the thermally cracked heavy oil is subjected to hydrogenation in a hydrogenation treatment process, and a hydrogenation-treated oil of a necessary fraction (or a necessary fraction in the thermally cracked heavy oil may be fractionated in advance and then subjected to hydrogenation) is obtained. However, in order to treat the thermally cracked heavy oil by hydrogenation until hydrogenation cracking occurs, a large amount of hydrogen is required, and also, when a completely hydrogenated thermally cracked heavy oil is used as a feedstock, the BTX yield decreases, while the kerosene/diesel fraction is produced to a large extent. Therefore, in the cracking reforming reaction process based on a contact reaction with a catalyst for monocyclic aromatic hydrocarbon production that will be described below, the production efficiency of BTX is decreased to a very low level.

Furthermore, the amount of heat generation of the hydrogenation cracking reaction of the thermally cracked heavy oil is very large, and the operation of actual hydrogenation treatment apparatuses also becomes difficult. Moreover, since the boiling point range of the thermally cracked heavy oil is broad, and there are many heavy polycyclic aromatic hydrocarbons with 3 or more rings, there is a problem that the production efficiency for BTX in the cracking reforming reaction process is decreased to a very low level.

As such, it has been thought that it is difficult to efficiently produce BTX from thermally cracked heavy oil. However, the inventors conducted thorough investigations, and as a result, the inventors finally invented a new method for producing BTX from thermally cracked heavy oil very efficiently.

That is, in the present embodiment, primarily bicyclic aromatic hydrocarbons in the thermally cracked heavy oil are selectively hydrogenated and are converted to monocyclic aromatic hydrocarbons (naphthenobenzenes) having only one aromatic ring hydrogenated. Thereafter, the fraction obtained by converting to monocyclic aromatic hydrocarbons is brought into contact with a catalyst containing a crystalline aluminosilicate at a low pressure in the absence of molecular hydrogen to react therewith, and thus a cracking reforming reaction is carried out. Thereby, BTX is produced. Here, examples of the monocyclic aromatic hydrocarbons include indane, tetralin, and alkylbenzenes.

According to this method, since the amount of hydrogen needed to obtain BTX from thermally cracked heavy oil becomes minimal, the amount of hydrogen consumption can be suppressed, and also, the amount of heat generation, which is a serious problem, can also be suppressed. For example, when naphthalene which is a representative example of bicyclic aromatic hydrocarbons is hydrogenated to decalin, the amount of hydrogen consumption per mole of naphthalene is 5 moles; however, when naphthalene is hydrogenated to tetralin, hydrogen consumption per mole of naphthalene can be realized with an amount of 2 moles. Furthermore, there is a large fraction containing indenes in the thermally cracked heavy oil, but the amount of hydrogen consumption needed to hydrogenate this fraction to indanes is smaller than the amount needed to hydrogenate naphthalene to tetralin. Therefore, according to the method described above, bicyclic aromatic hydrocarbons in the thermally cracked heavy oil can be converted to naphthenobenzenes more efficiently.

Furthermore, in regard to the heavy fraction that consumes a large amount of hydrogen when thermally cracked heavy oil is subjected to hydrogenation, and adversely affect the performance of the catalyst for monocyclic aromatic hydrocarbon production that will be described below, it is preferable to have the heavy fraction separated by distillation in a distillation column as shown in FIG. 1 and removed in advance from the feedstock to be formed. In regard to the separation by distillation in a distillation column, for example, the boiling point of 400° C. is defined as the cut temperature, and the thermally cracked heavy oil is separated into a light fraction and a heavy fraction. By having the thermally cracked heavy oil separated as such, BTX can be produced more efficiently. The cut temperature used to perform separation by distillation is preferably 300° C. to 350° C., and more preferably 210° C. to 300° C.

Meanwhile, in regard to such separation by distillation using a distillation column, as shown by broken-line arrows in FIG. 1, the separation may be carried out in a later stage instead of an earlier stage of the hydrogenation treatment process. Also in that case, since a heavy fraction is separated from the thermally cracked heavy oil obtained after a hydrogenation treatment, and a light fraction is used as the feedstock, the adverse effect of the heavy fraction as described above can be prevented.

As such, the fraction (light fraction) of a thermally cracked heavy oil obtained by separating and removing a heavy fraction and subjecting the remaining fraction to hydrogenation can be efficiently converted to BTX by a contact reaction with the catalyst for monocyclic aromatic hydrocarbon production according to the present embodiment. Furthermore, since this light fraction also produces hydrogen by a BTX production reaction, this hydrogen can also be utilized again in the hydrogenation treatment of thermally cracked heavy oil.

The hydrogenation treatment of the thermally cracked heavy oil can be carried out by a known hydrogenation reactor. In this hydrogenation treatment using a hydrogenation reactor, the hydrogen partial pressure at the reactor inlet port is preferably 0.7 MPa to 20 MPa. The lower limit is more preferably 1 MPa or greater, even more preferably 1.5 MPa or greater, and still more preferably 2 MPa or greater. Furthermore, the upper limit is more preferably 15 MPa or less, and even more preferably 10 MPa or less. When the hydrogen partial pressure is less than 0.7 MPa, extensive coke production occurs on the catalyst, and the catalyst life is shortened. On the other hand, when the hydrogen partial pressure is greater than 20 MPa, the construction cost for the reactor and peripheral equipment increases, and there may be a lack of economic efficiency.

The LHSV (Liquid Hourly Space Velocity) in the hydrogenation treatment of the thermally cracked heavy oil is preferably 0.05 $h^{-1}$ to 2 $h^{-1}$. The lower limit is more preferably 0.1 $h^{-1}$ or higher, and even more preferably 0.2 $h^{-1}$ or higher. Also, the upper limit is more preferably 1.9 $h^{-1}$ or lower, and even more preferably 1.8 $h^{-1}$ or lower. When the LHSV is lower than 0.05 $h^{-1}$, an enormous construction cost for a reactor is required, and there may be a lack of economic efficiency. On the other hand, when the LHSV is higher than 2 $h^{-1}$, the hydrogenation treatment of thermally cracked heavy oil may not be sufficiently achieved, and the reactivity in the cracking reforming reaction process may be deteriorated.

The reaction temperature in the hydrogenation treatment of the thermally cracked heavy oil is preferably 200° C. to 450° C. The lower limit is more preferably 220° C. or higher, and even more preferably 250° C. or higher. Also, the upper limit is more preferably 440° C. or lower, and even more preferably 430° C. or lower. When the reaction temperature is lower than 200° C., there is a tendency that the hydrogenation treatment of the thermally cracked heavy oil is not sufficiently achieved. On the other hand, when the reaction temperature is higher than 450° C., since the generation of gas components as side products increases, the yield of hydrogenation-treated oil is decreased, and it is not preferable.

The hydrogen/oil ratio in the hydrogenation treatment of the thermally cracked heavy oil is preferably 100 NL/L to 2000 NL/L. The lower limit is more preferably 110 NL/L or higher, and even more preferably 120 NL/L or higher. Also, the upper limit is more preferably 1800 NL/L or lower, and even more preferably 1500 NL/L or lower. When the hydrogen/oil ratio is lower than 100 NL/L, coke production proceeds on the catalyst at the reactor outlet, and the catalyst life tends to be shortened. On the other hand, when the hydrogen/oil ratio is higher than 2000 NL/L, an enormous construction cost for a recycle compressor is required, and there may be a lack of economic efficiency.

The reaction mode for the hydrogenation treatment of thermally cracked heavy oil is not particularly limited, but usually the reaction mode can be selected from various processes such as fixed bed processes and mobile bed processes, and among them, fixed bed processes are preferred.

Also, the reactor is preferably a column-like reactor.

The catalyst for hydrogenation treatment used in the hydrogenation treatment of thermally cracked heavy oil contains at least one metal selected from the metals of Group 6 in the Periodic Table of Elements, and at least one metal selected from the metals of Group 8 to Group 10 of the Periodic Table of Elements. Preferred examples of the metals of Group 6 of the Periodic Table of Elements include molybdenum, tungsten and chromium, and particularly preferred examples include molybdenum and tungsten. Preferred examples of the metals of Group 8 to Group 10 of the Periodic Table of Elements include iron, cobalt and nickel, and more preferred examples include cobalt and nickel. These metals may be respectively used alone, or two or more kinds may also be used in combination. Regarding specific examples of the combination of metals, molybdenum-cobalt, molybdenum-nickel, tungsten-nickel, molybdenum-cobalt-nickel, and tungsten-cobalt-nickel are preferably used.

Meanwhile, the Periodic Table of Elements as used herein refers to the long form Periodic Table of Elements defined by the International Union of Pure and Applied Chemistry (IUPAC).

The catalyst for hydrogenation treatment is preferably a catalyst in which the aforementioned metals are supported on an inorganic carrier containing aluminum oxide. Preferred examples of the inorganic carrier containing aluminum oxide include alumina, alumina-silica, alumina-boria, alumina-titania alumina-zirconia, alumina-magnesia, alumina-silica-zirconia, alumina-silica-titanic, or carriers produced by adding porous inorganic compounds such as various clay minerals such as various zeolites, sepiolites and montmorillonites, to alumina. Among them, alumina is particularly preferred.

The catalyst for hydrogenation treatment is preferably a catalyst obtainable by supporting, on an inorganic carrier containing aluminum oxide, at least one metal selected from the metals of Group 6 of the Periodic Table of Elements in an amount of 10 mass % to 30 mass %, and at least one metal selected from the metals of Group 8 to Group 10 in an amount of 1 mass % to 7 mass %, relative to the total catalyst mass which is the total mass of the inorganic carrier and the metals. When the supporting amount of the metal of Group 6 of the Periodic Table of Elements or the supporting amount of the metal of Group 8 to Group 10 of the Periodic Table of Elements is less than the corresponding lower limit, there is a tendency that the catalyst does not exhibit sufficient hydrogenation treatment activity. On the other hand, when the supporting amounts are respectively greater than the upper limits, the catalyst cost increases, and aggregation of the supported metals and the like are prone to occur. Also, there is a tendency that the catalyst does not exhibit sufficient hydrogenation treatment activity.

There are no limitations on the precursor of the metal species used when the aforementioned metals are supported on the inorganic carrier, but inorganic salts, organic metal compounds and the like of the metals are used, and water-soluble inorganic salts are preferably used. In the supporting process, it is preferable to carry out the supporting process by using a solution, preferably an aqueous solution, of these metal precursors. Regarding the supporting operation, for example, known methods such as an immersion method, an impregnation method, and a co-precipitation method are preferably employed.

A carrier having the metal precursors supported thereon is dried, and then is calcined preferably in the presence of oxygen. It is preferable that the metal species be first converted to oxides. Furthermore, it is preferable to convert the metal species to sulfides, before the hydrogenation treatment of the thermally cracked heavy oil is carried out, by a sulfurization treatment called preliminary sulfurization.

The conditions for preliminary sulfurization are not particularly limited, but the process is preferably carried out such that a sulfur compound is added to a petroleum distillate fraction or a thermally cracked heavy oil (hereinafter, referred to as preliminary sulfurization feedstock), and this mixture is continuously brought into contact with the catalyst for hydrogenation treatment under the conditions of a temperature of 200° C. to 380° C., a LHSV of 1 $h^{-1}$ to 2 $h^{-1}$, at the same pressure as that employed at the time of operating the hydrogenation treatment, and for a treatment time of 48 hours or longer. The sulfur compound that is added to the preliminary sulfurization feedstock is not limited, but dimethyl disulfide (DMDS), sulfazole, hydrogen sulfide and the like are preferred. These are preferably added to the preliminary sulfurization feedstock in an amount of about 1 mass % relative to the mass of the preliminary sulfurization feedstock.

(Hydrogenation-Treated Oil of Thermally Cracked Heavy Oil)

The hydrogenation-treated oil of the thermally cracked heavy oil related to the method for producing aromatic hydrocarbons of the present embodiment, which is obtainable by the hydrogenation treatment described above, preferably has the following characteristics.

The distillation characteristics are such that the 10 vol % distillation temperature (T10) is from 140° C. to 200° C., while the 90 vol % distillation temperature (T90) is from 200° C. to 380° C.; and more preferably, T10 is from 160° C. to 190° C., while T90 is from 210° C. to 350° C. When T10 is lower than 140° C., there is a possibility that the feedstock formed by including this hydrogenation-treated oil may contain xylene which is one of the target substances, and therefore, it is not preferable. On the other hand, when T90 is higher than 380° C. (becoming heavy), it is not preferable from the viewpoints that the catalyst performance is decreased by metal poisoning to the catalyst for hydrogenation treatment, coke precipitation and the like; coke precipitation on the catalyst for monocyclic aromatic hydrocarbon production increases so that predetermined performance is not attained; and the amount of hydrogen consumption increases, making the process economically inefficient.

In order to hydrogenate the thermally cracked heavy oil related to the production of aromatic hydrocarbons of the present embodiment, in most cases, separation by distillation using a distillation column or the like is needed as described above. However, as described above, the thermally cracked heavy oil may be separated by distillation and then hydrogenated in the hydrogenation treatment process, or the thermally cracked heavy oil may be hydrogenated in the hydrogenation treatment process and then separated by distillation. From the viewpoint of efficiently utilizing hydrogen, it is preferable to subject the thermally cracked heavy oil to separation by distillation and then to a hydrogenation treatment.

In regard to the extent of the hydrogenation treatment of the thermally cracked heavy oil, there are no particular limitations as long as hydrogenation of polycyclic aromatic hydrocarbons in the thermally cracked heavy oil has progressed, but from the viewpoint of the reaction for BTX production that will be described below, it is preferable that the thermally cracked heavy oil that has been hydrogenation-treated, that is, the hydrogenation-treated oil, which is included in the feedstock supplied to this reaction for production, have the following characteristics.

Regarding this hydrogenation-treated oil (hydrogenation-treated oil of the thermally cracked heavy oil included in the feedstock), the content of the monocyclic aromatic hydrocarbons that are contained in the hydrogenation-treated oil is preferably 30 mass % or greater, and more preferably 50 mass % or greater. The monocyclic aromatic hydrocarbons as used herein mean hydrocarbons having one aromatic ring, such as alkylbenzenes and naphthenobenzenes. When the content of the monocyclic aromatic hydrocarbons is less than 30 mass %, BTX cannot be efficiently produced, and it is not preferable.

Furthermore, this hydrogenation-treated oil is such that the content of the polycyclic aromatic hydrocarbons having 2 or more rings that are contained in the hydrogenation-treated oil is preferably 50 mass % or less, more preferably 30 mass % or less, and even more preferably 20 mass % or less. Among the polycyclic aromatic hydrocarbons, the content of polycyclic aromatic hydrocarbons having 3 or more rings is preferably 20 mass % or less, more preferably 10 mass % or less, and even more preferably 5 mass % or less. When the content of the polycyclic aromatic hydrocarbons having 2 or more rings is greater than 50 mass %, BTX cannot be efficiently produced, and it is not preferable.

Furthermore, regarding this hydrogenation-treated oil, there are no particular limitations on the content of naphthene-based hydrocarbons that are contained in the hydrogenation-treated oil, but the content is preferably 50 mass % or less, and more preferably 30 mass % or less. When the content of the naphthene-based hydrocarbons is greater than 50 mass %, the amount of hydrogen consumption in the hydrogenation treatment process for the thermally cracked heavy oil becomes excessively large, and it is economically inefficient. Also, the amount of gas generation in the BTX production process (cracking reforming reaction process) increases, and the efficiency is decreased, which is not preferable.

Furthermore, regarding this hydrogenation-treated oil, the content of hydrocarbons having an indane skeleton and an indene skeleton that are contained in the hydrogenation-treated oil is preferably 5 mass % or greater, more preferably 10 mass % or greater, and even more preferably 20 mass % or greater. The upper limit of the content of the hydrocarbons having an indane skeleton and an indene skeleton is not particularly limited, but the upper limit is preferably 90 mass % or less. Since thermally cracked heavy oil is mainly a side product originating from a thermal cracking reaction of naphtha or the like, unlike the petroleum fractions obtainable by contact cracking or the like (LCO and the like), the thermally cracked heavy oil contains a large amount of hydrocarbons having an indene skeleton. The hydrocarbons having this indene skeleton serve as a satisfactory raw material for BTX production even when hydrogenated and converted to hydrocarbons having an indane skeleton, and also, the amount of hydrogen consumption is also small as compared with the process of converting naphthalene to tetralin. Therefore, it is preferable that the hydrocarbons having the indene skeleton be contained to a large extent (5 mass % or more) in the hydrogenation-treated oil of the thermally cracked heavy oil.

Examples of the hydrocarbons having an indane skeleton include indane, methylindane, ethylindane, dimethylindane, diethylindane, and the like. In the present embodiment, it is particularly preferable if the hydrogenation-treated oil contains indane and methylindane. Examples of the hydrocarbons having an indene skeleton include indene, methylindene, ethylindene, dimethylindene, diethylindene, and the like. In the present embodiment, it is particularly preferable if the hydrogenation-treated oil contains indene and methylindene.

Meanwhile, the content of monocyclic aromatic hydrocarbons, the content of polycyclic aromatic hydrocarbons, the content of naphthene-based hydrocarbons, and the content of hydrocarbons having an indane skeleton and an indene skeleton mean contents that are measured by an FID gas chromatography analysis.

(Base Material that can be Used as Mixture with Hydrogenation-Treated Oil of Thermally Cracked Heavy Oil)

In the present embodiment, the hydrogenation-treated oil of the thermally cracked heavy oil described above is essentially included as a feedstock, but if necessary, one kind or two or more kinds of distillate oils produced in a FCC apparatus (LCO, heavy cycle oil (HCO), clarified oil (CLO) and the like), fractions obtained by partially hydrogenating distillate oils produced in a FCC apparatus (partially hydrogenated LCO, partially hydrogenated HCO, partially hydrogenated CLO, and the like), distillate oils produced in a coker, fractions obtained by partially hydrogenating distillate oils produced in a coker, hydrogenated cracked fractions containing a large amount of naphthene components, cracked oil fractions produced in a heavy oil hydrogenation cracking apparatus or a heavy oil hydrogenation desulfurization apparatus, fractions obtained by hydrogenating the fractions obtainable from oil sand, and the like may be mixed with the hydrogenation-treated oil and used as a feedstock.

However, even in the case of forming a feedstock by mixing such base materials other than the hydrogenation-treated oil, the feedstock thus obtainable is prepared such that the end point of the distillation characteristics is 400° C. or lower as described above.

As such, when a feedstock including a hydrogenation-treated oil of the thermally cracked heavy oil obtainable from an ethylene production apparatus is obtained, in the present embodiment, this feedstock is sent to a cracking reforming reaction process as shown in FIG. 1 and is brought into contact with a catalyst for monocyclic aromatic hydrocarbon production to produce BTX.

(Catalyst for Monocyclic Aromatic Hydrocarbon Production)

The catalyst for monocyclic aromatic hydrocarbon production contains a crystalline aluminosilicate.

[Crystalline Aluminosilicate]

From the viewpoint of further increasing the yield of BTX, the crystalline aluminosilicate is preferably a zeolite with medium-sized pores and/or a zeolite with large-sized pores.

The zeolite with medium-sized pores is a zeolite having a 10-membered ring skeletal structure, and examples of the zeolite with medium-sized pores include zeolites having AEL type, EUO type, FER type, HEU type, MEL type, MFI type, NES type, TON type, and WEI type crystal structures. Among these, MFI type zeolite is preferred from the viewpoint of further increasing the yield of BTX.

The zeolite with large-sized pores is a zeolite having a 12-membered ring skeletal structure, and examples of the zeolite with large-sized pores include zeolites having AFI type, ATO type, BEA type, CON type, FAU type, GME type, LTL type, MOR type, MTW type, and OFF type crystal structures. Among these, BEA type, FAU type and MOR type zeolites are preferred from the viewpoint of being industrially usable, and BEA type zeolite is more preferred from the viewpoint of further increasing the yield of BTX.

The crystalline aluminosilicate may also include a zeolite with small-sized pores having a 10-membered or fewer-membered ring skeletal structure, or a zeolite with ultralarge-sized pores having a 14-membered ring or more-membered ring skeletal structure, in addition to the zeolite with medium-sized pores and the zeolite with large-sized pores.

Here, examples of the zeolite having small-sized pores include zeolites having ANA type, CHA type, ERI type, GIS type, KFI type, LTA type, NAT type, PAU type and YUG type crystal structures.

Examples of the zeolite with ultralarge-sized pores include zeolites having CLO type and VPI type crystal structures.

When the cracking reforming reaction process is carried out as a fixed bed reaction, the content of the crystalline aluminosilicate in the catalyst for monocyclic aromatic hydrocarbon production is preferably 60 mass % to 100 mass %, more preferably 70 mass % to 100 mass %, and particularly preferably 90 mass % to 100 mass %, when the total amount of the catalyst for monocyclic aromatic hydrocarbon production is designated as 100 mass %. When the content of the crystalline aluminosilicate is 60 mass % or more, the yield of BTX can be sufficiently increased.

When the cracking reforming reaction process is carried out as a fluidized bed reaction, the content of the crystalline aluminosilicate in the catalyst for monocyclic aromatic hydrocarbon production is preferably 20 mass % to 60 mass %, more preferably 30 mass % to 60 mass %, and particularly preferably 35 mass % to 60 mass %, when the total amount of the catalyst for monocyclic aromatic hydrocarbon production is designated as 100 mass %. When the content of the crystalline aluminosilicate is 20 mass % or more, the yield of BTX can be sufficiently increased. When the content of the crystalline aluminosilicate is more than 60 mass %, the content of a binder that may be incorporated into the catalyst is decreased, and the catalyst may not be suitable for fluidized bed applications.

[Phosphorus and Boron]

The catalyst for monocyclic aromatic hydrocarbon production preferably contains phosphorus and/or boron. When the catalyst for monocyclic aromatic hydrocarbon production contains phosphorus and/or boron, a decrease in the BTX yield over time can be prevented, and coke production on the catalyst surface can be suppressed.

Examples of the method for incorporating phosphorus to the catalyst for monocyclic aromatic hydrocarbon production include an ion exchange method and an impregnation method. Specific examples include a method of supporting phosphorus on a crystalline aluminosilicate, a crystalline aluminogallosilicate, or a crystalline aluminozincosilicate; a method of incorporating a phosphorus compound at the time of zeolite synthesis and substituting a portion in the skeleton of a crystalline aluminosilicate with phosphorus; and a method of using a crystallization accelerator containing phosphorus at the time of zeolite synthesis. The phosphate ion-containing aqueous solution used at that time is not particularly limited, but solutions prepared by dissolving phosphoric acid, diammonium hydrogen phosphate, ammonium dihydrogen phosphate, and other water-soluble phosphates in water at arbitrary concentrations can be preferably used.

Examples of the method of incorporating boron into the catalyst for monocyclic aromatic hydrocarbon production include an ion exchange method and an impregnation method. Specific examples include a method of supporting boron on a crystalline aluminosilicate, a crystalline aluminogallosilicate or a crystalline aluminozincosilicate; a method of incorporating a boron compound at the time of zeolite synthesis and substituting a portion of the skeleton of a crystalline aluminosilicate with boron; and a method of using a crystallization accelerator containing boron at the time of zeolite synthesis.

The content of phosphorus and/or boron in the catalyst for monocyclic aromatic hydrocarbon production is preferably 0.1 mass % to 10 mass %, relative to the total weight of the catalyst, and the lower limit is more preferably 0.5 mass % or more, while the upper limit is more preferably 9 mass % or less, and particularly preferably 8 mass % or less. When the content of phosphorus and/or boron relative to the total weight of the catalyst is 0.1 mass % or more, a decrease in the yield of BTX over time can be prevented, and when the content is 10 mass % or less, the yield of BTX can be increased.

[Gallium and Zinc]

In the catalyst for monocyclic aromatic hydrocarbon production, gallium and/or zinc can be incorporated as necessary. When gallium and/or zinc is incorporated, the production proportion of BTX can be further increased.

The form of gallium incorporation in the catalyst for monocyclic aromatic hydrocarbon production may be a form in which gallium is incorporated into the lattice skeleton of a crystalline aluminosilicate (crystalline aluminogallosilicate), a form in which gallium is supported on a crystalline aluminosilicate (gallium-supporting crystalline aluminosilicate), or both of them.

The form of zinc incorporation in the catalyst for monocyclic aromatic hydrocarbon production may be a form in which zinc is incorporated into the lattice skeleton of a crystalline aluminosilicate (crystalline aluminozincosilicate), a form in which zinc is supported on a crystalline aluminosilicate (zinc-supporting crystalline aluminosilicate), or both of them.

The crystalline aluminogallosilicate and crystalline aluminozincosilicate have a structure in which $SiO_4$, $AlO_4$ and $GaO_4$/$ZnO_4$ structures exist in the skeletal structure. Furthermore, the crystalline aluminogallosilicate and crystalline aluminozincosilicate are obtained by, for example, gel crystallization based on hydrothermal synthesis, or a method of inserting gallium or zinc into the lattice skeleton of a crystalline aluminosilicate. Furthermore, the crystalline aluminogallosilicate and crystalline aluminozincosilicate are obtained by a method of inserting aluminum into the lattice skeleton of a crystalline gallosilicate or a crystalline zincosilicate.

The gallium-supporting crystalline aluminosilicate is a compound in which gallium is supported on a crystalline aluminosilicate according to a known method such as an ion exchange method or an impregnation method. The gallium source that is used at that time is not particularly limited, but examples thereof include gallium salts such as gallium nitrate and gallium chloride, and gallium oxide.

The zinc-supporting crystalline aluminosilicate is a compound in which zinc is supported on a crystalline aluminosilicate according to a known method such as an ion exchange method or an impregnation method. The zinc source that is used at that time is not particularly limited, but examples thereof include zinc salts such as zinc nitrate and zinc chloride, and zinc oxide.

When the catalyst for monocyclic aromatic hydrocarbon production contains gallium and/or zinc, the content of gallium and/or zinc in the catalyst for monocyclic aromatic hydrocarbon production is preferably 0.01 mass % to 5.0 mass %, and more preferably 0.05 mass % to 2.0 mass %, relative to 100 mass % of the total amount of the catalyst. When the content of gallium and zinc is 0.01 mass % or greater, the production proportion of BTX can be further increased. When the content is 5.0 mass % or less, the yield of BTX can be further increased.

[Shape]

The catalyst for monocyclic hydrocarbon production is produced into, for example, a powder form, a particulate form, a pellet form or the like according to the reaction mode. For example, in the case of a fluidized bed, the catalyst is produced in a powder form, and in the case of a fixed bed, the catalyst is produced in a particulate form or a pellet form. The average particle size of the catalyst used in a fluidized bed is preferably 30 μm to 180 μm, and more preferably 50 μm to 100 μm. Furthermore, the apparent density of the catalyst used in a fluidized bed is preferably 0.4 g/cc to 1.8 g/cc, and more preferably 0.5 g/cc to 1.0 g/cc.

Meanwhile, the average particle size represents the particle size for a proportion of 50 mass % in a particle size distribution obtained by classification using sieves, and the apparent density is a value measured by the method of JIS Standards R9301-2-3.

When a particulate or pellet-like catalyst is obtained, if necessary, an oxide which is inert to the catalyst is incorporated as a binder, and the mixture may be molded by using various molding machines.

When the catalyst for monocyclic aromatic hydrocarbon production contains an inorganic oxide such as a binder, a binder containing phosphorus may also be used.

(Reaction Mode)

In the present embodiment, examples of the reaction mode employed when the feedstock is brought into contact with a catalyst for monocyclic aromatic hydrocarbons to react therewith, include a fixed bed, a mobile bed, and a fluidized bed. According to the present embodiment, since a heavy component (a hydrogenation-treated oil of a thermally cracked heavy oil) is used as a feedstock, a fluidized bed which is capable of continuously removing the coke component adhering to the catalyst and is capable of stably carrying out the reaction is preferred; and a continuously regenerative type fluidized bed in which a catalyst is circulated between a reactor and a regenerator so that reaction-regeneration can be continuously repeated, is particularly preferred. When brought into contact with the catalyst, the feedstock is preferably in a gas phase. Furthermore, the feedstock may also be diluted with a gas as necessary. Furthermore, when unreacted feedstock occurs, the raw material may be recycled as necessary.

(Reaction Temperature)

The reaction temperature at the time of bringing the feedstock into contact with the catalyst to react therewith is not particularly limited, but the reaction temperature is preferably 350° C. to 700° C., and more preferably 450° C. to 650° C. When the reaction temperature is lower than 350° C., the reaction activity is not sufficient. When the reaction temperature is higher than 700° C., it is disadvantageous in terms of energy, and catalyst regeneration and the like are difficult.

(Reaction Pressure)

The reaction pressure employed when the feedstock is brought into contact with the catalyst to react therewith is 0.1 MPaG to 1.5 MPaG. That is, the contact between the feedstock and the catalyst for monocyclic aromatic hydrocarbon production related to the present embodiment is carried out at a pressure of 0.1 MPaG to 1.5 MPaG.

In the present embodiment, since the reaction idea is completely different from the conventional methods based on hydrogenation cracking, the high pressure conditions that are considered important in hydrogenation cracking are not required. Rather, a pressure higher than needed accelerates cracking and produces undesired light gas as a side product, and therefore, it is not preferable. Furthermore, not requiring high pressure conditions is preferential even in terms of reaction apparatus design. On the other hand, the main purpose of the present embodiment lies in active utilization of a hydrogen transfer reaction, and it was found that in this regard, the pressurized conditions are preferential to normal pressure or reduced pressure conditions. That is, when the reaction pressure is 0.1 MPaG to 1.5 MPaG, a hydrogen transfer reaction can be efficiently carried out.

(Contact Time)

The contact time between the feedstock and the catalyst for monocyclic aromatic hydrocarbon production is not particularly limited so long as the desired reaction substantially proceeds. However, for example, the time for gas passage on the catalyst for monocyclic aromatic hydrocarbon production is preferably 1 second to 300 seconds, and the lower limit is more preferably 5 seconds or longer, while the upper limit is more preferably 150 seconds or shorter. When the contact time is 1 second or longer, the reaction can be performed reliably, and when the contact time is 300 seconds or shorter, accumulation of carbon substances on the catalyst caused by coking or the like can be suppressed. The amount of generation of light gas caused by cracking can also be suppressed.

EXAMPLES

Hereinafter, the invention will be more specifically described based on Examples and Comparative Examples, but the invention is not intended to be limited to these Examples.

[Method for Producing Hydrogenation-Treated Oil of Thermally Cracked Heavy Oil]

(Production of Catalyst for Hydrogenation Treatment)

Water glass No. 3 was introduced into 1 kg of an aqueous solution of sodium aluminate at a concentration of 5 mass %, and the mixture was placed in a container that had been kept warm at 70° C. Furthermore, a solution prepared by adding an aqueous solution of titanium (IV) sulfate (24 mass % in terms of $TiO_2$ content) to 1 kg of an aqueous solution of aluminum sulfate at a concentration of 2.5 mass %, was prepared in another container that had been kept warm at 70° C., and this solution was added dropwise to the aqueous solution containing sodium aluminate for 15 minutes. The amounts of the water glass and the aqueous solution of titanium sulfate were adjusted such that predetermined contents of silica and titania would be obtained.

The time point at which the pH of the mixed solution reached 6.9 to 7.5 was designated as the end point, and the slurry product thus obtained was collected by filtration through a filter. Thus, a cake-like slurry was obtained. This cake-like slurry was transferred into a container equipped with a reflux cooler, 300 ml of distilled water and 3 g of a 27% aqueous ammonia solution were added thereto, and the mixture was heated and stirred at 70° C. for 24 hours. The slurry obtained after the stirring treatment was introduced into a kneading apparatus, and the slurry was heated to a temperature of 80° C. or higher and kneaded while moisture was removed. Thus, a clay-like kneading product was obtained.

The kneading product thus obtained was extruded in a cylinder form having a diameter of 1.5 mm by using an extruder, and the extrusion product was dried at 110° C. for 1 hour and then calcined at 550° C. to obtain a molded carrier. 300 g of the molded carrier thus obtained was collected, and the molded carrier was impregnated by spraying with an impregnating solution prepared by adding molybdenum trioxide, cobalt (II) nitrate hexahydrate and phosphoric acid (concentration 85%) to 1.50 ml of distilled water, and adding malic acid until the salts were dissolved.

The amounts of molybdenum trioxide, cobalt (II) nitrate hexahydrate, and phosphoric acid used were adjusted such that predetermined supporting amounts would be obtained. The sample impregnated with the impregnating solution was dried for 1 hour at 110° C. and then calcined at 550° C., and thus a catalyst A was obtained. The catalyst A had a content of $SiO_2$ of 1.9 mass % and a content of $TiO_2$ of 2.0 mass % on the basis of the carrier mass, and had a supporting amount of $MoO_3$ of 22.9 mass %, a supporting amount of CoO of 2.5 mass % and a supporting amount of $P_2O_5$ of 4.0 mass % on the basis of the catalyst mass.

(Separation by Distillation of Thermally Cracked Heavy Oil)

A thermally cracked heavy oil A obtainable from an ethylene production apparatus as shown in Table 1 was subjected to a distillation operation to separate a light fraction only, and thus a light-thermally cracked heavy oil B and a light-thermally cracked heavy oil C as shown in Table 2 were prepared. The boiling point ranges of the light-thermally cracked heavy oil B and the light-thermally cracked heavy oil C thus prepared are described in Table 2.

TABLE 1

|  |  | Thermally cracked heavy oil A |
|---|---|---|
| Density(@15° C.) | g/cm³ | 1.052 |
| Dynamic viscosity (@50° C.) | mm²/s | 28.11 |
| Sulfur content | mass ppm | 500 |
| Distillation characteristics |  |  |
| IBP | ° C. | 195 |
| T10 | ° C. | 201 |
| T90 | ° C. | 505 |
| EP | ° C. | 602 |
| Aromatic content | vol % | 87 |

TABLE 2

|  |  | Light-thermally cracked heavy oil B | Light-thermally cracked heavy oil C |
|---|---|---|---|
| Distillation characteristics |  |  |  |
| IBP | ° C. | 182 | 185 |
| T10 | ° C. | 195 | 198 |
| T90 | ° C. | 212 | 264 |
| EP (End point) | ° C. | 230 | 288 |
| Content of monocyclic aromatic hydrocarbons | mass % | 56 | 42 |
| Content of polycyclic aromatic hydrocarbons with 2 or more rings | mass % | 36 | 52 |
| (Among them, content of polycyclic aromatic hydrocarbons with 3 or more rings) | mass % | 1 or less | 1 or less |
| Content of methylindene and methylindanes | mass % | 34 | 27 |

(Hydrogenation Treatment Reaction of Thermally Cracked Heavy Oil)

A fixed bed continuous flow type reaction apparatus was packed with the catalyst A, and first, preliminary sulfurization of the catalyst was carried out. That is, to a fraction corresponding to straight run light oil (preliminarily sulfurized feedstock), which has a density at 15° C. of 851.6 kg/m³, an initial distillation point of 231° C. and an end distillation point of 376° C. in a distillation test, a sulfur content of 1.18 mass % in terms of sulfur atoms based on the mass of the preliminarily sulfurized feedstock, and a color of L1.5, 1 mass % of DMDS based on the mass of the fraction was added, and this mixture was continuously supplied to the catalyst A for 48 hours.

Thereafter, a hydrogenation treatment was carried out by using the light-thermally cracked heavy oil B and the light-thermally cracked heavy oil C indicated in Table 2 as feedstocks, under the conditions of a reaction temperature of 350° C., a LHSV of 0.5 h⁻¹, a hydrogen/oil ratio of 750 NL/L, and a pressure as indicated in Table 3. The respective characteristics of the hydrogenation-treated oils B-1, B-2, C-1, C-2 and C-3 of the thermally cracked heavy oil thus obtained are described in Table 3.

TABLE 3

| Feedstock |  | Hydrogenation-treated oil B-1 Light-thermally cracked heavy oil B | Hydrogenation-treated oil B-2 Light-thermally cracked heavy oil B | Hydrogenation-treated oil C-1 Light-thermally cracked heavy oil C | Hydrogenation-treated oil C-2 Light-thermally cracked heavy oil C | Hydrogenation-treated oil C-3 Light-thermally cracked heavy oil C |
|---|---|---|---|---|---|---|
| Hydrogen partial pressure | MPa | 3 | 6 | 3 | 6 | 9 |
| Distillation characteristics |  |  |  |  |  |  |
| T10 | ° C. | 172 | 174 | 176 | 181 | 177 |
| T90 | ° C. | 218 | 220 | 267 | 254 | 240 |
| EP (End point) | ° C. | 235 | 240 | 296 | 290 | 282 |
| Saturated components | mass % | 10 | 14 | 8 | 12 | 34 |
| (Among them, content of naphthene-based hydrocarbons) | mass % | 2 | 6 | 2 | 6 | 29 |
| Content of monocyclic aromatic hydrocarbons | mass % | 80 | 82 | 77 | 80 | 63 |
| Content of polycyclic aromatic hydrocarbons with 2 or more rings | mass % | 10 | 4 | 15 | 8 | 3 |
| (among them, content of polycyclic aromatic hydrocarbons with 3 or more rings) | mass % | 1 or less | 1 or less | 1 or less | 1 or less | 1 or less |
| Content of methylindene and methylindanes | mass % | 33 | 32 | 26 | 24 | 22 |

The distillation characteristics shown in Tables 1, 2 and 3 were respectively measured according to "Petroleum products—Distillation testing methods" stipulated in JIS K 2254. Also, the density (@15° C.) of Table 1 was measured according to "Petroleum products—Distillation testing methods" stipulated in JIS K 2254. The dynamic viscosity (@50° C.) was measured according to "Crude oil and petroleum products—Dynamic viscosity testing methods and viscosity index calculation methods" stipulated in JIS K 2283. The sulfur content was measured according to "Crude oil and petroleum products—Sulfur content testing methods" stipulated in JIS K 2541.

Furthermore, the respective compositions shown in Tables 1, 2 and 3 were calculated, with respect to the saturated components and aromatic components obtained by silica gel chromatographic fractionation, by a hydrocarbon type analysis by performing a mass analysis according to an EI ionization method (apparatus: manufactured by JEOL, Ltd., JMS-700) according to ASTM D2425 "Standard Test Method for Hydrocarbon Types in Middle Distillates by Mass Spectrometry". Furthermore, the content of hydrocarbons having an indane skeleton and an indene skeleton was calculated by a FID gas chromatography analysis.

Method for Producing Aromatic Hydrocarbons

Preparation Example 1

For Catalyst for Monocyclic Aromatic Hydrocarbon Production

Preparation of Catalyst Containing Ga and Phosphorus-Supported Crystalline Aluminosilicate A solution (A) containing sodium silicate (J sodium silicate No. 3, $SiO_2$: 28 mass % to 30 mass %, Na: 9 mass % to 10 mass %, balance water, manufactured by Nippon Chemical Industrial Co., Ltd.): 1706.1 g and water: 2227.5 g, and a solution (B) containing $Al_2(SO_4)_3 \cdot 14\text{-}18H_2O$ (reagent grade, manufactured by Wako Pure Chemical Industries, Ltd.): 64.2 g, tetrapropylammonium bromide: 369.2 g, $H_2SO_4$ (97 mass %): 152.1 g, NaCl: 326.6 g and water: 2975.7 g were respectively prepared.

Subsequently, while the solution (A) was stirred at room temperature, the solution (B) was slowly added to the solution (A).

The mixture thus obtained was vigorously stirred for 15 minutes in a mixer, and the gel was crushed to obtain fine emulsion.

Subsequently, this mixture was placed in an autoclave made of stainless steel, and a crystallization operation was carried out under self-pressure under the conditions of a temperature of 165° C., a time of 72 hours, and a stirring speed of 100 rpm. After completion of the crystallization operation, the product was filtered to collect a solid product, and washing and filtration was repeated 5 times by using about 5 liters of deionized water. The solid obtained by filtration was dried at 120° C., and the solid was calcined at 550° C. for 3 hours under a stream of air.

It was confirmed by an X-ray diffraction analysis (model name: Rigaku RINT-2500V) that the calcination product thus obtained had an MFI structure. Furthermore, the $SiO_2/Al_2O_3$ ratio (molar ratio) obtained by a fluorescence X-ray analysis (model name: Rigaku ZSX101e) was 64.8. Furthermore, the content of the aluminum element contained in the lattice skeleton calculated from these results was 1.32 mass %.

Subsequently, a 30 mass % aqueous solution of ammonium nitrate was added at a ratio of 5 mL per 1 g of the calcination product thus obtained, and the mixture was heated and stirred at 100° C. for 2 hours, subsequently filtered and washed with water. This operation was repeated 4 times, and then the mixture was dried at 120° C. for 3 hours. Thus, an ammonium type crystalline aluminosilicate was obtained.

Thereafter, calcination was carried out for 3 hours at 780° C., and thus a proton type crystalline aluminosilicate was obtained.

Subsequently, 120 g of the proton type crystalline aluminosilicate thus obtained was impregnated with 120 g of an aqueous solution of gallium nitrate such that 0.4 mass % (a value calculated relative to 100 mass % of the total mass of the crystalline aluminosilicate) of gallium would be supported, and the resultant was dried at 120° C. Thereafter, the product was calcined at 780° C. for 3 hours under an air stream, and thus a gallium-supported crystalline aluminosilicate was obtained.

Subsequently, 30 g of the gallium-supported crystalline aluminosilicate thus obtained was impregnated with 30 g of an aqueous solution of diammonium hydrogen phosphate such that 0.7 mass % of phosphorus (a value calculated relative to 100 mass % of the total mass of the crystalline aluminosilicate) would be supported, and the resultant was dried at 120° C. Thereafter, the product was calcined at 780° C. for 3 hours under an air stream, and thus a catalyst containing a crystalline aluminosilicate, gallium and phosphorus was obtained. In order to exclude the influence of the catalyst thus obtained on the initial activity, the catalyst was subjected to a hydrothermal treatment at a treatment temperature of 650° C., a treatment time of 6 hours, and in an environment of 100 mass % of water vapor. Thereafter, the hydrothermal deterioration treated catalyst was tabletted by applying a pressure of 39.2 M Pa (400 kgf) to the catalyst thus obtained, and the catalyst was crude pulverized and adjusted to a 20 to 28 mesh size. Thus, a particulate catalyst B was obtained.

Preparation Example 2

For Catalyst for Monocyclic Aromatic Hydrocarbon Production

Preparation of Catalyst Containing Zn and Phosphorus-Supported Crystalline Aluminosilicate A solution (A) containing sodium silicate (J sodium silicate No. 3, $SiO_2$: 28 mass % to 30 mass %, Na: 9 mass % to 10 mass %, balance water, manufactured by Nippon Chemical Industrial Co., Ltd.): 1706.1 g and water: 2227.5 g, and a solution (B) containing $Al_2(SO_4)_3 \cdot 14\text{-}18H_2O$ (reagent grade, manufactured by Wako Pure Chemical Industries, Ltd.): 64.2 g, tetrapropylammonium bromide: 369.2 g, $H_2SO_4$ (97 mass %): 152.1 g, NaCl: 326.6 g and water: 2975.7 g were respectively prepared.

Subsequently, while the solution (A) was stirred at room temperature, the solution (B) was slowly added to the solution (A).

The mixture thus obtained was vigorously stirred for 15 minutes in a mixer, and the gel was crushed to obtain fine emulsion.

Subsequently, this mixture was placed in an autoclave made of stainless steel, and a crystallization operation was carried out under self-pressure under the conditions of a temperature of 165° C., a time of 72 hours, and a stirring speed of 100 rpm. After completion of the crystallization operation, the product was filtered to collect a solid product, and washing and filtration was repeated 5 times by using about 5 liters of deionized water. The solid obtained by filtration was dried at 120° C., and the solid was calcined at 550° C. for 3 hours under a stream of air.

It was confirmed by an X-ray diffraction analysis (model name: Rigaku RINT-2500V) that the calcination product thus obtained had an MFI structure. Furthermore, the $SiO_2/Al_2O_3$ ratio (molar ratio) obtained by a fluorescence X-ray analysis (model name: Rigaku ZSX101e) was 64.8. Furthermore, the content of the aluminum element contained in the lattice skeleton calculated from these results was 1.32 mass %.

Subsequently, a 30 mass % aqueous solution of ammonium nitrate was added at a ratio of 5 mL per 1 g of the calcination product thus obtained, and the mixture was heated and stirred at 100° C. for 2 hours, subsequently filtered and washed with water. This operation was repeated 4 times, and then the mixture was dried at 120° C. for 3 hours. Thus, an ammonium type crystalline aluminosilicate was obtained.

Thereafter, calcination was carried out for 3 hours at 780° C., and thus a proton type crystalline aluminosilicate was obtained.

Subsequently, 120 g of the proton type crystalline aluminosilicate thus obtained was impregnated with 120 g of an aqueous solution of zinc nitrate such that 0.4 mass % (a value calculated relative to 100 mass % of the total mass of the crystalline aluminosilicate) of zinc would be supported, and the resultant was dried at 120° C. Thereafter, the product was calcined at 780° C. for 3 hours under an air stream, and thus a zinc-supported crystalline aluminosilicate was obtained.

Subsequently, 30 g of the zinc-supported crystalline aluminosilicate thus obtained was impregnated with 30 g of an aqueous solution of diammonium hydrogen phosphate such that 0.7 mass % of phosphorus (a value calculated relative to 100 mass % of the total mass of the crystalline aluminosilicate) would be supported, and the resultant was dried at 120° C. Thereafter, the product was calcined at 780° C. for 3 hours under an air stream, and thus a catalyst containing a crystalline aluminosilicate, zinc and phosphorus was obtained. In order to exclude the influence of the catalyst thus obtained on the initial activity, the catalyst was subjected to a hydrothermal treatment at a treatment temperature of 650° C., a treatment time of 6 hours, and in an environment of 100 mass % of water vapor. Thereafter, the hydrothermal deterioration treated catalyst was tabletted by applying a pressure of 39.2 MPa (400 kgf) to the catalyst thus obtained, and the catalyst was crude pulverized and adjusted to a 20 to 28 mesh size. Thus, a particulate catalyst C was obtained.

Examples 1 to 6 and Comparative Examples 1 to 3

Preparation of Aromatic Hydrocarbons

Each of the feedstocks indicated in Table 4 was brought into contact with the corresponding catalyst to react therewith, by using a flow type reaction apparatus in which the catalyst B or C (10 ml) was packed in the reactor, under the conditions of a reaction temperature of 550° C. and a reaction pressure of 0.3 MPaG in the absence of molecular hydrogen. The combinations of the feedstock and catalyst thus used were designated as Examples 1 to 6 and Comparative Examples 1 to 3 as shown in Table 4. Meanwhile, when each of the feedstocks was brought into contact with the catalyst to react therewith, nitrogen was introduced as a diluent so that the contact time between the feedstock and the catalyst would be 10 seconds.

TABLE 4

| | Feedstock | Catalyst | BTX yield (mass %) |
|---|---|---|---|
| Comparative Example 1 | Thermally cracked heavy oil A | Catalyst B | 12 |
| Example 1 | Hydrogenation-treated oil B-1 | Catalyst B | 38 |
| Example 2 | Hydrogenation-treated oil B-2 | Catalyst B | 44 |
| Example 3 | Hydrogenation-treated oil B-2 | Catalyst C | 42 |
| Comparative Example 2 | Light-thermally cracked heavy oil B | Catalyst B | 21 |
| Example 4 | Hydrogenation-treated oil C-1 | Catalyst B | 33 |
| Example 5 | Hydrogenation-treated oil C-2 | Catalyst B | 40 |
| Example 6 | Hydrogenation-treated oil C-3 | Catalyst B | 42 |
| Comparative Example 3 | Light-thermally cracked heavy oil C | Catalyst B | 15 |

BTX was prepared by allowing the materials to react under these conditions for 30 minutes, and a composition analysis of the products was carried out by FID gas chromatography directly connected to the reaction apparatus, to thereby evaluate the catalyst activity in the early phase of the reaction. The evaluation results are show in Table 4.

From the results shown in Table 4, it was found that Examples 1 to 6 that used hydrogenation-treated oils of thermally cracked heavy oil having predetermined characteristics as the feedstock, can be produce BTX with high yield as compared with Comparative Examples 1 to 3 that used, as the feedstock, a thermally cracked heavy oil which was not subjected to a hydrogenation treatment.

Therefore, in Examples 1 to 6, it was confirmed that BTX can be efficiently produced from a feedstock containing a hydrogenation-treated oil of a thermally cracked heavy oil obtainable from an ethylene production apparatus, without incorporating molecular hydrogen.

Preferred embodiments of the invention have been described above, however the invention is not intended to be limited to these embodiments. Addition, deletion, substitution and other modifications of the constitution can be made to the extent that the gist of the invention is maintained. The invention is not intended to be limited by the descriptions disclosed above, and is intended to be limited only by the scope of the attached claims.

INDUSTRIAL APPLICABILITY

According to the method for producing aromatic hydrocarbons of the invention, BTX can be efficiently produced from a feedstock containing a hydrogenation-treated oil of a thermally cracked heavy oil obtainable from an ethylene production apparatus.

The invention claimed is:
1. A method for producing BTX (benzene, toluene, and xylenes), the method comprising the steps of:
   thermally cracking a raw material to produce an effluent comprising heavy oil and ethylene;
   separating the effluent to obtain the heavy oil;
   hydrogenating the heavy oil to obtain a feedstock comprising 8 mass % or less of polycyclic aromatic hydrocarbons with two or more rings and 50 mass % or more of monocyclic aromatic hydrocarbons, wherein the feedstock has a distillation end point temperature of 400° C. or lower; and contacting the feedstock with a cracking reforming catalyst comprising a crystalline aluminosilicate to produce BTX,
wherein the contacting of the feedstock with the cracking reforming catalyst is carried out under a pressure of 0.1 MPaG to 1.5 MPaG and a contact time between the feedstock and the catalyst is within a range of 5 seconds to 300 seconds.

2. The method according to claim 1, wherein the feedstock further comprises a content of hydrocarbons having an indane skeleton and an indene skeleton of 5 mass % or more.

3. The method according to claim 1, wherein:
the step of separating the effluent comprises separating by distillation the effluent to obtain the heavy oil; and
the step of hydrogenating the heavy oil is carried out in the presence of hydrogen and a hydrogenation catalyst under a hydrogen partial pressure of 0.7 MPa to 20 MPa, a LHSV of 0.05 h-1 to 2 h-1, a reaction temperature of 200° C. to 450° C., and a hydrogen/oil ratio of 100 NL/L to 2000 NL/L.

4. The method according to claim 3, wherein the hydrogenation catalyst comprises at least one metal selected from the metals of Group 6 of the Periodic Table of Elements in an amount of 10 mass % to 30 mass %, and at least one metal selected from the metals of Group 8 to Group 10 of the Periodic Table of Elements in an amount of 1 mass % to 7 mass %, relative to the total catalyst mass, supported on an inorganic carrier containing aluminum oxide.

5. The method according to claim 4, wherein the at least one metal selected from the metals of Group 6 of the Periodic Table of Elements is molybdenum and/or tungsten, and the at least one metal selected from the metals of Group 8 to Group 10 of the Periodic Table of Elements is cobalt and/or nickel.

6. The method according to claim 1, wherein:
the step of hydrogenating the heavy oil is carried out in the presence of hydrogen and a hydrogenation catalyst under a hydrogen partial pressure of 0.7 MPa to 20 MPa, a LHSV of 0.05 h-1 to 2 h-1, a reaction temperature of 200° C. to 450° C., and a hydrogen/oil ratio of 100 NL/L to 2000 NL/L; and
separating by distillation the hydrogenated heavy oil to obtain the feedstock.

7. The method according to claim 6, wherein the hydrogenation catalyst comprises at least one metal selected from the metals of Group 6 of the Periodic Table of Elements in an amount of 10 mass % to 30 mass %, and at least one metal selected from the metals of Group 8 to Group 10 of the Periodic Table of Elements in an amount of 1 mass % to 7 mass %, relative to the total catalyst mass, supported on an inorganic carrier containing aluminum oxide.

8. The method according to claim 7, wherein the at least one metal selected from the metals of Group 4 of the Periodic Table of Elements is molybdenum and/or tungsten, and the at least one metal selected from the metals of Group 8 to Group 10 of the Periodic Table of Elements is cobalt and/or nickel.

9. The method according to claim 1, wherein the cracking reforming catalyst contains gallium and/or zinc.

10. The method according to claim 1, wherein the cracking reforming catalyst contains phosphorus.

11. The method according to claim 1, wherein the feedstock is brought into contact with the cracking reforming catalyst in the absence of molecular hydrogen.

* * * * *